United States Patent
Okada et al.

(10) Patent No.: US 10,194,785 B2
(45) Date of Patent: Feb. 5, 2019

(54) INSERTION DEVICE AND INSERTION SYSTEM

(71) Applicant: OLYMPUS CORPORATION, Hachioji-shi, Tokyo (JP)

(72) Inventors: Hiromitsu Okada, Hachioji (JP); Atsushi Watanabe, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 36 days.

(21) Appl. No.: 15/369,174

(22) Filed: Dec. 5, 2016

(65) Prior Publication Data

US 2017/0079509 A1  Mar. 23, 2017

Related U.S. Application Data

(63) Continuation of application No. PCT/JP2015/065774, filed on Jun. 1, 2015.

(30) Foreign Application Priority Data

Jun. 5, 2014 (JP) ................................ 2014-117127

(51) Int. Cl.
*A61B 1/04* (2006.01)
*A61B 1/00* (2006.01)
(Continued)

(52) U.S. Cl.
CPC ............ *A61B 1/00082* (2013.01); *A61B 1/00* (2013.01); *A61B 1/00006* (2013.01);
(Continued)

(58) Field of Classification Search
CPC .................... A61B 1/00135; A61B 1/00154
(Continued)

(56) References Cited

U.S. PATENT DOCUMENTS 5,569,159 A * 10/1996 Anderson .......... A61B 1/00142
600/114
5,941,815 A * 8/1999 Chang ................ A61B 1/00142
600/114
(Continued)

FOREIGN PATENT DOCUMENTS

JP  S61-284226 A  12/1986
JP  H07-227378 A  8/1995
(Continued)

OTHER PUBLICATIONS

Apr. 5, 2016 Office Action issued in Japanese Patent Application No. 2015-560422.
(Continued)

*Primary Examiner* — Matthew J Kasztejna
(74) *Attorney, Agent, or Firm* — Oliff PLC

(57) ABSTRACT

The insertion device includes an insertion portion that is inserted into a lumen, a fixing portion that is provided at an insertion part of the insertion portion to be inserted into the lumen, and fixes the insertion portion at a first position inside of the lumen, and a positioning portion that is attached to a part of the insertion portion exposed to the external of the lumen and provided in the outer part of the lumen. The positioning portion positions the insertion portion at a second position outside of the lumen.

18 Claims, 18 Drawing Sheets

(51) Int. Cl.
*A61B 1/31* (2006.01)
*A61B 17/02* (2006.01)

(52) U.S. Cl.
CPC ............ *A61B 1/00154* (2013.01); *A61B 1/31* (2013.01); *A61B 17/02* (2013.01)

(58) Field of Classification Search
USPC .................................. 600/114–115, 121–125
See application file for complete search history.

(56) References Cited

U.S. PATENT DOCUMENTS

| | | | | |
|---|---|---|---|---|
| 6,451,041 | B1* | 9/2002 | Moenning | A61B 17/3417 604/164.04 |
| 6,793,621 | B2* | 9/2004 | Butler | A61B 1/00154 600/114 |
| 6,869,393 | B2* | 3/2005 | Butler | A61B 1/00151 600/114 |
| 8,460,186 | B2* | 6/2013 | Ortiz | A61B 17/3421 600/216 |
| 9,155,550 | B2* | 10/2015 | Shipp | A61B 17/34 |
| 9,662,139 | B2* | 5/2017 | Shipp | A61B 17/34 |
| 2002/0147385 | A1 | 10/2002 | Butler et al. | |
| 2006/0264707 | A1* | 11/2006 | Kinney | A61B 1/00151 600/115 |
| 2011/0144442 | A1* | 6/2011 | Farrell | A61B 1/32 600/206 |

FOREIGN PATENT DOCUMENTS

| | | |
|---|---|---|
| JP | 2004-524903 A | 8/2004 |
| JP | 2008-272302 A | 11/2008 |
| JP | 2011-156230 A | 8/2011 |
| JP | 2012-000270 A | 1/2012 |

OTHER PUBLICATIONS

Jun. 23, 2015 International Search Report issued in Patent Application No. PCT/JP2015/065774.

Dec. 15, 2016 International Preliminary Report on Patentability issued in International Application No. PCT/JP2015/065774.

\* cited by examiner

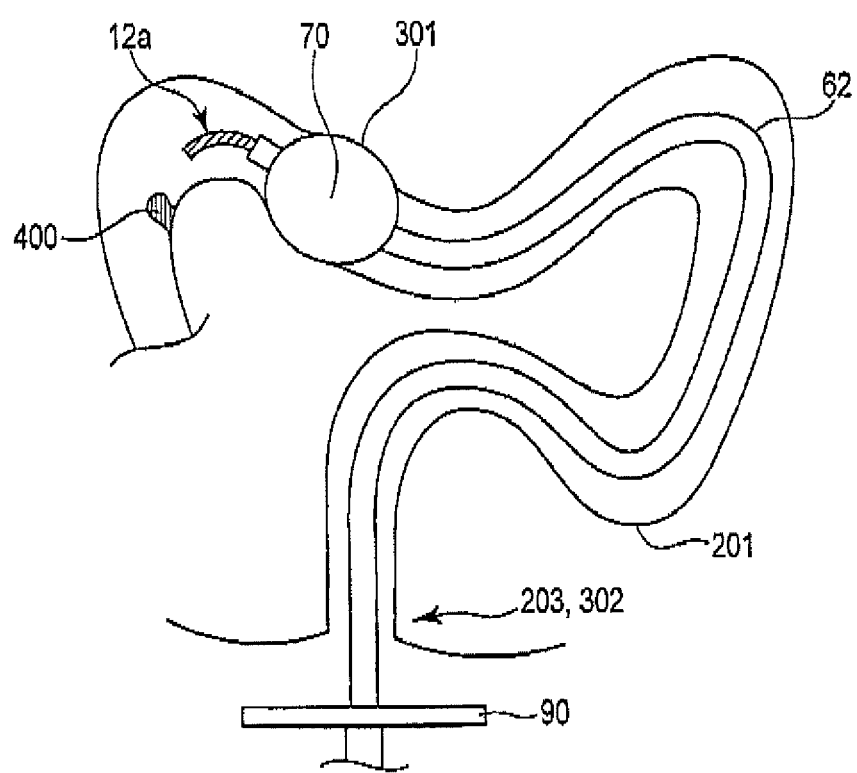
F I G. 4A

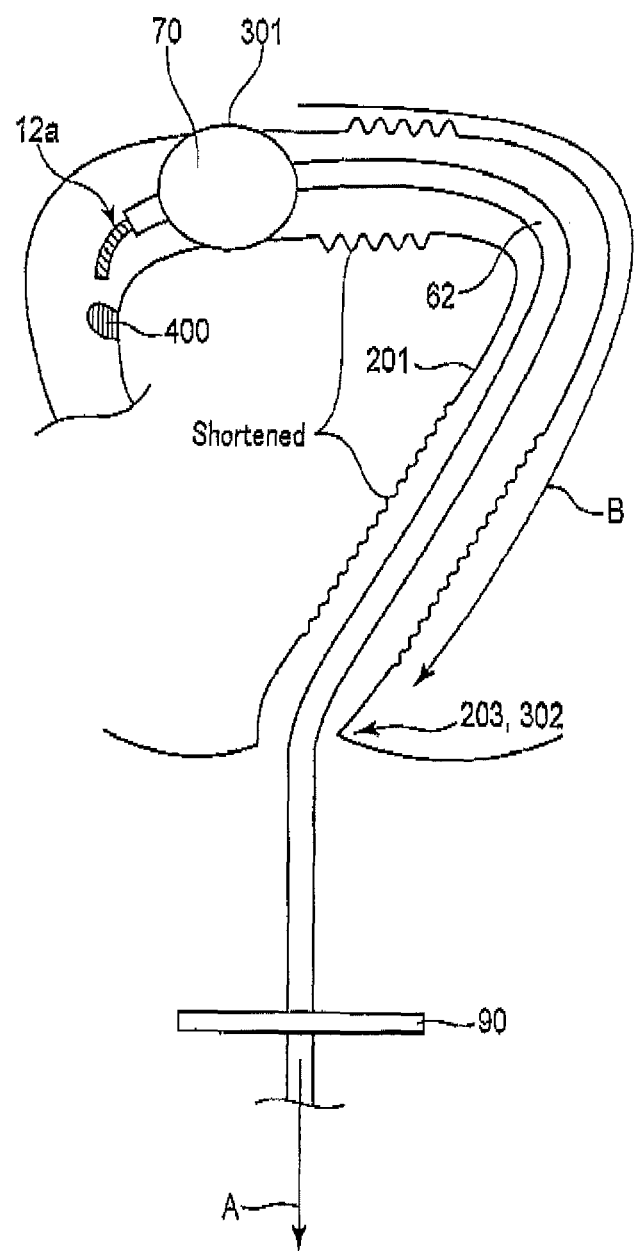
F I G. 4B

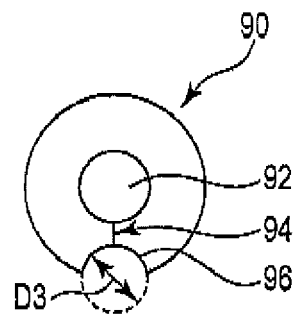
F I G. 5A
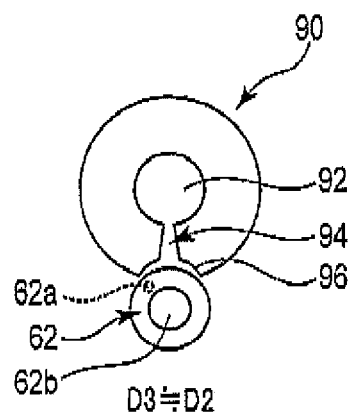
F I G. 5B
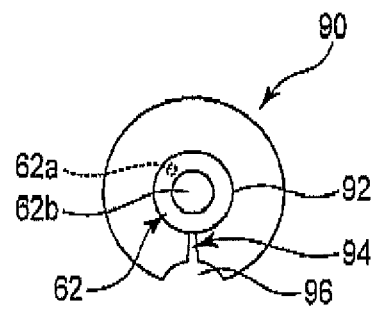
F I G. 5C

Contracted state

Expanded state $D8 < D4 < D5 \fallingdotseq D7 < D9$ $D8 < D4 < D5 \fallingdotseq D7 < D9$

D8<D4<D5≒D7<D9

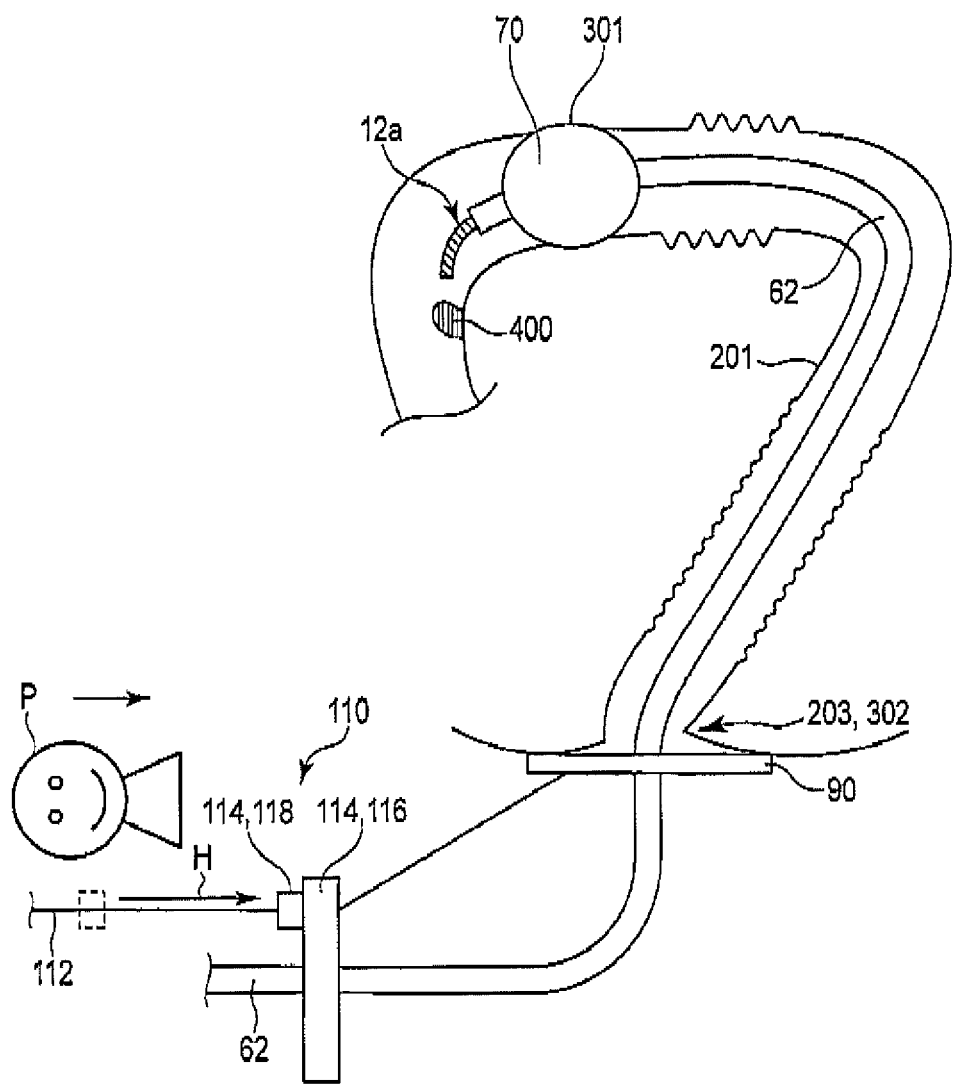
F I G. 10K

INSERTION DEVICE AND INSERTION SYSTEM

CROSS-REFERENCE TO RELATED APPLICATIONS

This application is a Continuation Application of PCT Application No. PCT/JP2015/065774, filed Jun. 1, 2015 and based upon and claiming the benefit of priority from prior Japanese Patent Application No. 2014-117127, filed Jun. 5, 2014, the entire contents of all of which are incorporated herein by reference.

BACKGROUND OF THE INVENTION

1. Field of the Invention

The present invention relates to generally to an insertion device to be inserted into a body cavity and an insertion system.

2. Description of the Related Art

For example, Jpn. Pat. Appln. KOKAI Publication No. 61-284226 discloses an insertion device that it used for improving insertional performance of an insertion portion and workability of an endoscope to a lumen when the insertion portion of the endoscope is inserted into a meandering lumen such as a large intestine. The insertion device has an expandable and contractible balloon that is provided on an outer peripheral surface of a distal end portion of the insertion device, when the insertion device is inserted into the lumen, the expanded balloon is brought into pressure contact with an inner surface of the lumen so that the insertion device does not slide in the lumen, but is fixed to the inside of the lumen.

BRIEF SUMMARY OF THE INVENTION

In an aspect of the insertion device of the present invention, the insertion device is inserted into a lumen, and is positioned relative to both of a first position inside of the lumen and a second position outside of the lumen; the insertion device includes an insertion portion that is inserted into the lumen, a fixing portion that is provided at an insertion part of the insertion portion to be inserted into the lumen and fixes the insertion portion to the lumen at the first position, and a positioning portion that is attached to a part exposed externally to the lumen and provided in the outer part of the lumen and positions the insertion portion at the second position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4A illustrates the state where a fixing portion is fixed to a lumen at a first position.

FIG. 4 illustrates the state where the insertion portion including the fixing portion is pulled, a force toward an entrance from the first position is applied to the lumen through the fixing portion from the insertion portion, and the lumen is shortened (compressed) by the force.

FIG. 5A is a front view of a positioning portion in the first modification.

FIG. 5B illustrates where the positioning portion shown in FIG. 5A is to be attached to the insertion portion.

FIG. 5C illustrates where the positioning portion shown in FIG. 5A has been attached to the insertion portion.

FIG. 10K illustrates the state where a contact maintenance portion slides along the actuation portion to be in contact with the main portion and to be fixed to the actuation portion so that the actuation portion maintains a state which the tension is applied, and the insertion portion is positioned adjacent to the peripheral region of the entrance while the state is controlled.

DETAILED DESCRIPTION OF THE INVENTION

Hereinafter, embodiments of the present invention will be described with reference to the drawings.

First Embodiment

Structure

A first embodiment will be described with reference to FIG. 1, FIG. 2, FIG. 3A, FIG. 3B, FIG. 3C, FIG. 4A, FIG. 4B, and FIG. 4C. Some elements in some of the drawings will be omitted for simplification.

[Insertion System 10]

Figure 1:
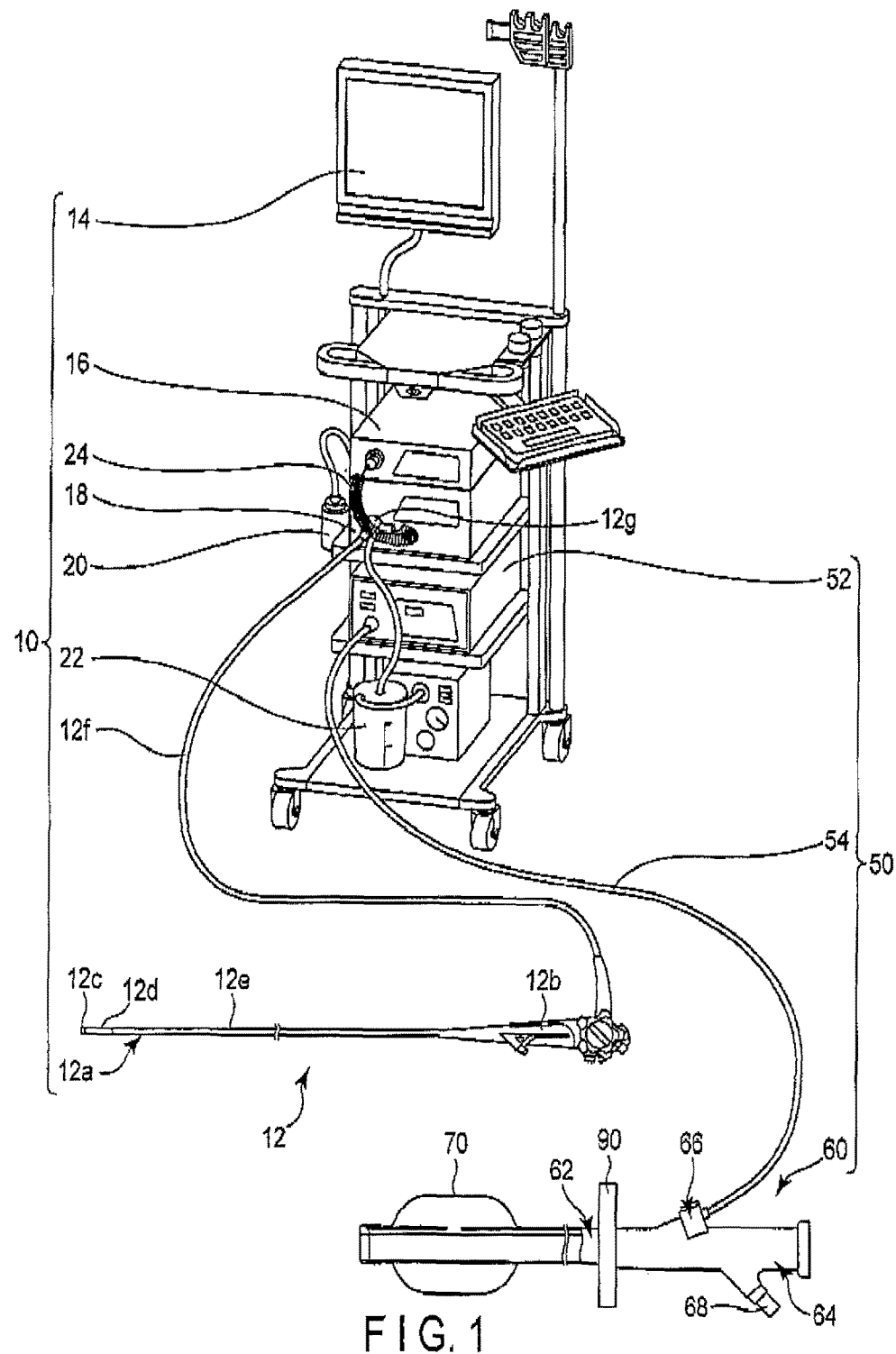
FIG. 1 is a schematic view of an insertion system according to the present invention.

As shown in FIG. 1, an insertion system 10 includes an endoscope 12, a monitor 14, a video processor 16, a light source apparatus 18, an air-supply/water-supply tank 20, a suction pump 22, a signal cable 24, and an insertion assistance unit 50.

The endoscope 12 includes an insertion portion 12a that is inserted into a subject, for example, a lumen such as an intestinal tract, and an operation portion 12b coupled to a proximal end portion of the insertion portion 12a. The insertion portion 12a includes a distal hard portion 12c, a bendable portion 12d, and a flexible tube portion 12e from a distal end portion of the insertion portion 12a to the proximal end portion in the order given. The flexible tube portion 12e is coupled to the operation portion 12b. The endoscope 12 includes a universal cord 12f extending from the operation portion 12b, and a connector 12g which is disposed at an end of the universal cord 12f and connectable to the light source device 18.

The video processor 16 is electrically connected to the connector 12g thorough the signal cable 24. The video processor 16 controls an image sensor (not shown in the drawings) disposed in the insertion portion 12a through the signal cable 24, and processes an image signal of a lumen imaged by the image sensor. The image signal processed by the video processor 16 is displayed on the monitor 14 as an endoscope image.

The light source device 18 supplies illumination light to a known light guide (not shown in the drawings) disposed within the endoscope 12.

The air-supply/water-supply tank 20 is used when air or liquid is supplied to a known air-supply/water-supply duct not shown in the drawings. The air-supply/water-supply duct is disposed within the endoscope 12, and is connected to the air-supply/water-supply tank 20 through a tube not shown in the drawings.

The suction pump 22 is used when liquid or tissue within a lumen is sucked through a known suction duct not shown in the drawings. The suction duct is disposed within the endoscope 12, and is connected to the suction pump 22 through a tube not shown in the drawings.

[Insertion Assistance Unit 50]

As shown in FIG. 1, the insertion assistance unit 50 includes a first fluid pump 52 that supplies and drains fluid, and a first fluid supply-drainage tube 54 which is connected to the first fluid pump 52 and through which fluid passes. The insertion assistance unit 50 also includes a second fluid pump (not shown in the drawings) that supplies and drains fluid, and a second fluid supply-drainage tube (not shown in the drawings) which is connected to the second fluid pump and through which fluid passes.

[Insertion Device 60]

As shown in FIG. 1, FIG. 2, FIG. 4A, FIG. 4B, and FIG. 4C, the insertion assistance unit 50 further includes an insertion device 60 that is inserted into a lumen 201, and is positioned relative to both of a first position 301 inside of the lumen 201, and a second position 302 outside of the lumen 201. For example, when a distal end portion of the insertion device 60 is inserted into the lumen 201, a proximal end portion of the insertion device 60 is disposed an outside of the lumen 201, and an operation portion 64 of the insertion device 60 is grasped in the outside of the lumen 201. The insertion device 60 of the present embodiment acts as an over-tube and a catheter, for example. In the present embodiment, the insertion device 60 is independent from the endoscope 12.

As shown in FIG. 1, FIG. 2, FIG. 4A, FIG. 4B, and FIG. 4C, the insertion device 60 includes an elongated insertion portion 62 to be inserted into the lumen 201, and the operation portion 64 that is disposed at a proximal end portion of the insertion portion 62 and operates the insertion portion 62. The operation portion 64 is also a grasping portion to be grasped by an operator, and performs insertion-removal operation of the insertion portion 62 while being grasped. The insertion device 60 includes a first connection portion 66 disposed at the proximal end portion of the insertion portion 62 and connected to the first fluid supply-drainage tube 54, and a second connection portion 68 disposed at the proximal end portion of the insertion portion 62 and connected to the second fluid supply-drainage tube not shown in the drawings.

Figure 2:
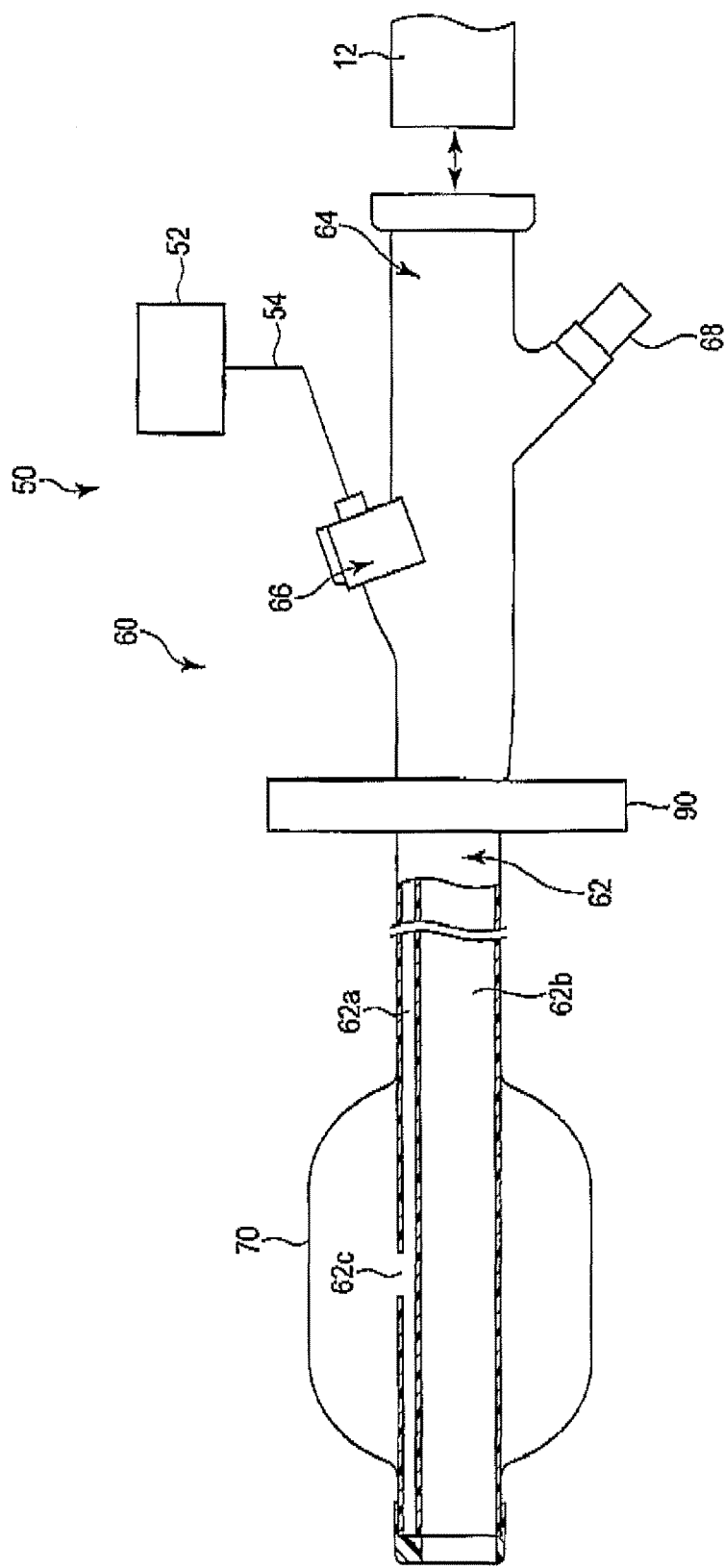
FIG. 2 is a schematic view of an insertion assistance unit in the first embodiment.

When the insertion device 60 acts as an over-tube, the insertion portion 62 acts as a main body of the over-tube. The insertion portion 62 acts as a soft multi-lumen tube, for example. As shown in FIG. 2, the insertion portion 62 includes a first hollow portion 62a communicating with the first connection portion 66, and a second hollow portion 62b communicating with the second connection portion 68. The first fluid pump 52 supplies and drains fluid to the first hollow portion 62a through the first fluid supply-drainage tube 54 and the first connection portion 66. For example, the insertion portion 12a is inserted and removed through the second hollow portion 62b. The first hollow portion 62a is independent from the second hollow portion 62b, and thinner than the second hollow portion 62b. A distal end of the first hollow portion 62a is not opened to the exterior, but communicates with a fixing portion 70 described later. A distal end of the second hollow portion 62b is opened to the exterior, but does not communicate with the fixing portion 70. The insertion device 60 can supply fluid into the lumen 201 or suck fluids and solids from the lumen 201 through the second fluid pump and the second fluid supply-drainage tube not shown in the drawings, and through the second connection portion 68 and the second hollow portion 62b. The first hollow portion 62a has at least one opening portion 62c disposed at part of a peripheral surface of the insertion portion 62 and is opened to the exterior. The first hollow portion 62a communicates with the exterior through the opening portion 62c.

For example, fluid such as water is supplied from the second connection portion 68 to the second hollow portion 62b to improve lubrication of the outer surface of the insertion portion 12a relative to the inner surface of the second hollow portion 62b. A mechanism of supplying fluid may be a syringe, instead of a pump.

As shown in FIG. 1, FIG. 2, FIG. 3A, FIG. 3B, FIG. 3C, FIG. 4A, FIG. 4B, and FIG. 4C, the insertion device 60 includes the fixing portion 70 disposed at the distal end portion of the insertion portion 62, and a positioning portion 90 attached to the proximal end portion of the insertion portion 62 and disposed the outside of the lumen 201. The distal end portion of the insertion portion 62 is an insertion part of the insertion portion 62 to be inserted inside the lumen 201. The proximal end portion of the insertion portion 62 is an exposed part of the insertion portion 62 disposed the outside of the lumen 201 and exposed to the external.

The insertion portion 62, the fixing portion 70, and the positioning portion 90 are formed of an elastic member having biocompatibility, for example. Such an elastic member is formed of resin material such as a silicon rubber, a fluorine rubber, and a thermoplastic elastomer such as polyurethane, for example.

[Fixing Portion 70]

As shown in FIG. 2, both end portions of the fixing portion 70 in an axial direction of the insertion device 60 are bonded on an outer peripheral surface of the insertion portion 62 in the state where the fixing portion 70 covers the entire surface of the distal end portion of the insertion portion 62. In this case, the fixing portion 70 covers the opening portion 62c, and an internal spatial portion of the fixing portion 70 communicates with the first hollow portion 62a through the opening portion 62c. The fixing portion 70 has a balloon that is expanded and contracted by supply or drainage when fluid is drained from the first fluid pump 52 to the fixing portion 70 through the first fluid supply-drainage tube 54, the first connection portion 66, the first hollow portion 62a, and the opening portion 62c. Specifically, the fixing portion 70 expands if gas is supplied to the internal spatial portion of the fixing portion 70, and contracts if gas is emitted from the internal spatial portion of the fixing portion 70, for example.

[Positioning Portion 90]

Figure 3A:
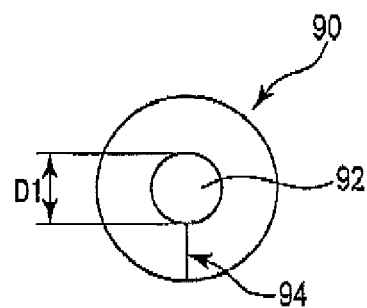
FIG. 3A is a front view of a positioning portion in the first embodiment.
Figure 3B:
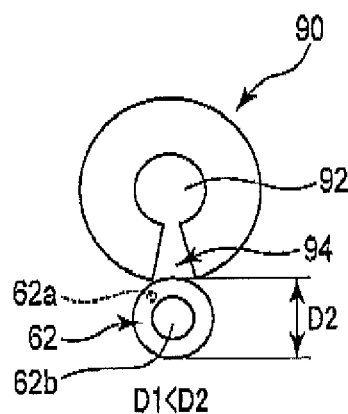
FIG. 3B illustrates the state where the positioning portion shown in FIG. 3A is to be attached to an insertion portion.
Figure 3C:
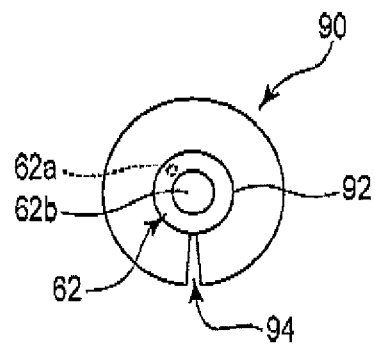
FIG. 3C illustrates the state where the positioning portion shown in FIG. 3A has been attached to the insertion portion.

As shown in FIG. 3A, FIG. 3B, and FIG. 3C, the positioning portion 90 includes a first through hole 92 that passes through the positioning portion 90 in a thickness direction of the positioning portion 90. The first through hole 92 is provided at a center of the positioning portion 90. The positioning portion 90 is formed, for example, as a ring shape. If the first through hole 92 is provided, the external shape of the positioning portion 90 is not particularly limited. The first through hole 92 is formed so that the insertion portion 62 passes through the positioning portion 90 in the thickness direction of the positioning portion 90. For example, the first through hole 92 of the present embodiment (inside diameter D1 of the positioning portion 90) is minutely smaller than an outside diameter D2 of the insertion portion 62.

As shown in FIG. 3A, FIG. 3B, and FIG. 3C, the positioning portion 90 further includes a notching portion 94 formed toward an outer peripheral surface of the positioning portion 90 from the first through hole 92 so that the insertion portion 62 is inserted into the first through hole 92 from the outer peripheral surface of the positioning portion 90. The notching portion 94 is formed toward the outer peripheral surface from the first through hole 92 so that the insertion portion 62 is inserted from the outer peripheral surface of the positioning portion 90 into the first through hole 92 that is formed to be smaller than the outside diameter of the insertion portion 62 to allow the insertion portion 62 to pass through. The notching portion 94 is provided linearly along the radial direction of the positioning portion 90, and is formed as a slit shape, for example.

As shown in FIG. 3A, FIG. 3B, and FIG. 3C, when the insertion portion 62 is inserted into the first through hole 92 through the notching portion 94 from the outer peripheral surface of the positioning portion 90, the positioning portion 90 is attached on the insertion portion 62 in the state where an inner peripheral surface of the positioning portion 90 is in contact with an outer peripheral surface of the insertion portion 62. The insertion portion 62 is pushed toward the notching portion 94 so as to widen the notching portion 94 when the positioning portion 90 is in contact with the insertion portion 62. The insertion portion 62 is inserted into the first through hole 92 by widening the notching portion 94. It is suitable that the positioning portion 90 is attached on the insertion portion 62 before the insertion portion 62 is inserted into the lumen 201, for example. However, the timing of attaching is not limited thereto.

As shown in FIG. 3A, FIG. 3B, and FIG. 3C, the first through hole 92 (inside diameter D1 of the positioning portion 90) is formed to be minutely smaller than the outside diameter D2 of the insertion portion 62 so that the inner peripheral surface of the positioning portion 90 is ensured to be in contact with the outer peripheral surface of the insertion portion 62. The positioning portion 90 has a desired thickness, and a wide contact area is ensured by the thickness. Accordingly, as shown in FIG. 2, when the positioning portion 90 is attached into the insertion portion 62, the positioning portion 90 is brought into contact with, and positioned relative to, the insertion portion 62. In other words, the positioning portion 90 ensures a fixing force by which the positioning portion 90 is fixed to the insertion portion 62. If a force equal to or greater than the fixing force (contacting force) is applied to the positioning portion 90 in the axial direction of the insertion portion 62, for example, the positioning portion 90 is slidable relative to the insertion portion 62 in the axial direction of the insertion portion 62. The positioning portion 90 is slidable relative to the insertion portion 62 in the axial direction of the insertion portion 62, and has a fixing force to be positioned at an entrance 203 and fixed to the insertion portion 62 in the state where the positioning portion 90 is in contact with a peripheral region of the entrance 203 of the lumen 201 by an elongation force of the lumen 201 as described below.

The positioning portion 90 is detached from the insertion portion 62 if the insertion portion 62 is removed externally from the first through hole 92 through the notching portion 94. The positioning portion 90 is detachable and attachable relative to the insertion portion 62.

Figure 4C:
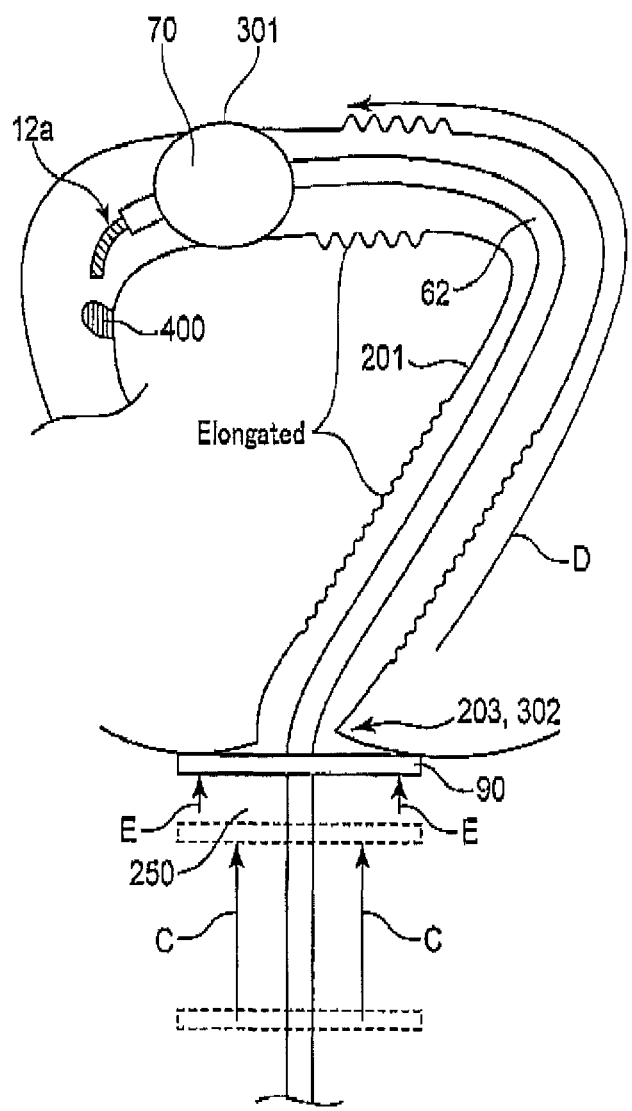
FIG. 4C illustrates where the positioning portion is pressed onto a peripheral region of the entrance of the lumen by elongation of the lumen to be brought into contact with the peripheral region of the entrance and to be positioned at the entrance of the lumen, the state and the length of the lumen from the first position to the entrance are defined, the lumen is also positioned from the first position to the entrance, the state and the length of the insertion portion from the first position to the entrance are defined, and the insertion portion is positioned from the first position to the entrance.

As shown in FIG. 4A, FIG. 4B, and FIG. 4C, the outside diameter of the positioning portion 90 is larger than the outside diameter D2 of the insertion portion 62 and the entrance 203, for example, an anus.

[Fixing of Fixing Portion 70]

After the contracted fixing portion 70 is inserted into the meandering lumen 201 (for example, the large intestine) together with the distal end portion of the insertion portion 62, the fixing portion 70 is expanded by fluid at the desired first position 301 within the lumen 201, as shown in FIG. 4A. It is confirmed that the distal end portion of the insertion portion 62 including the fixing portion 70 reaches the first position 301, for example, by visual observation through X-ray penetration, movement of the insertion device 60, and the length of the insertion device 60 exposed from the lumen 201.

As shown in FIG. 4A, the fixing portion 70 is expanded, is brought into contact with the lumen 201 at the first position 301 within the lumen 201, and is directly fixed to the lumen 201 at the first position 301, so that the insertion portion 62 is fixed to the lumen 201 at the first position 301. Specifically, when the fixing portion 70 is brought into contact with the lumen 201, the fixing portion 70 is fixed to the lumen 201 by a friction generated between the fixing portion 70 and the lumen 201 in the direction of pulling the insertion portion 62 (axial direction) which is a direction along a insertion direction of the insertion portion 62.

For example, the fixing portion 70 is expanded to be brought into contact with an internal wall (inner peripheral surface) of the lumen 201, and is directly in pressure contact with the internal wall, as shown in FIG. 4A. The fixing portion 70 is fixed by pressure-contact.

Although it is not shown in the drawings, the fixing portion 70 may be provided between folds of the lumen 201 and expanded to be fixed therebetween, for example. In this case, the fixing portion 70 reaches between the folds before expansion, and the folds are present in the front and the rear of the fixing portion 70. The fixing portion 70 is expanded and brought into contact with the folds in the front and the rear of the fixing portion 70. In this state, the insertion portion 62 is pulled so that the expanded fixing portion 70 is directly caught in the folds and fixed.

The fixing portion 70 is prevented from moving in the axial direction of the insertion device 60 by the pressure-contact and by being caught; in other words, the fixing portion 70 is fixed. As a result, the distal end portion of the insertion device 60 is fixed within the lumen 201.

[Positioning of Positioning Portion 90]

In the state where the fixing portion 70 is fixed, as described above, the meandering lumen 201 itself is movable relative to the inside of the body, and can be shortened and elongated in the axial direction of the lumen 201. That is, the lumen 201 is movable from the first position 301 to the entrance 203 of the lumen 201, for example, an anus, and the state and the length of the lumen 201 are variable. The state of the lumen 201 indicates a bending shape of the lumen 201, for example.

As shown in FIG. 4A and FIG. 4B, when the fixing portion 70 is fixed into the lumen 201, the insertion portion 62 including the fixing portion 70 is pulled as shown by an arrow A in FIG. 4B. By this operation, a force toward the entrance 203 from the first position 301 is applied to the lumen 201 through the fixing portion 70 from the insertion portion 62. Then, as shown by an arrow B in FIG. 4B, the lumen 201 is pulled from the first position 301 which is a starting point toward the entrance 203, and the lumen 201 is shortened (compressed).

That is, as shown in FIG. 4B, when the fixing portion 70 is fixed to the lumen 201, the lumen 201 is pulled from the first position 301 toward the entrance 203 by pulling the insertion portion 62. When the lumen 201 is pulled from the first position 301 toward the entrance 203, the force is applied to the lumen 201 that can be elongated and shortened from the first position 301 toward the entrance 203 (in the direction where the lumen 201 is shortened). The lumen 201 is shortened from the first position 301 toward the entrance 203 by the force.

Accordingly, as shown in FIG. 4B, the state of the lumen 201 (bending shape) and the length of the lumen 201 are temporarily and desirably maintained (controlled) in the shortened state. That is, the lumen 201 is temporarily prevented from moving relative to the body, and is temporarily fixed. The movement of the insertion device 60 in the removal direction of the insertion device 60 is prevented by fixing of the fixing portion 70 and temporal fixing of the shortened lumen 201.

Next, as shown by an arrow C in FIG. 4C, a force equal to or stronger than the fixing force of the positioning portion 90 is applied to the positioning portion 90 attached to the insertion portion 62 in the axial direction of the insertion device 60. The positioning portion 90 slides along the insertion portion 62 in the axial direction of the insertion device 60. The positioning portion 90 moves close to the entrance 203 by the slide. In the axial direction of the insertion portion 62, a space portion 250 is generated between the positioning portion 90 and the entrance 203. It is desirable that a distance between the positioning portion 90 and the entrance 203 at the space portion 250 is short. If the force equal to or stronger than the fixing force is released, the positioning portion 90 is positioned to an insertion portion 61 while being located close to the entrance 203 by the fixing force. The slide may be performed in the state where the notching portion 94 is widened.

In the state where the positioning portion 90 is positioned, the shortened lumen 201 is elongated due to an elastic force of the lumen 201 itself generated as counterforce at the lumen 201 in the opposite direction of pulling, as shown by an arrow D in FIG. 4C. For example, the lumen 201 is elongated from the entrance 203 as the starting point to return to the state shown in FIG. 4A. In other words, the lumen 201 will return to its original state. The insertion portion 62 fixed in the lumen 201 by the fixing portion 70 is inserted into (pulled into) the lumen 201 by elongation of the lumen in the direction indicated by an arrow D. In this case, the positioning portion 90 attached to the insertion portion 62 also moves toward the entrance 203 as indicated by an arrow E. The positioning portion 90 is directly pushed to the peripheral region of the entrance 203 by elongation of the lumen 201, and is in direct contact with the peripheral region of the entrance 203 by elongation of the lumen 201. That is after the positioning portion 90 is positioned at the first position 301, the positioning portion 90 positioned to the insertion portion 62 is positioned at the entrance 203 of the lumen 201 which is the outside of the lumen 201. The positioning portion 90 positions the insertion portion 62 at the second position 302. The positioning portion 90 is in direct contact with the peripheral region of the entrance 203, and accordingly, the space portion 250 disappears. By the contact, insertion of the insertion portion 62 to the lumen 201 is stopped, and the lumen 201 stops elongation after the lumen 201 is elongated by the length of the space portion 250. Accordingly, the lumen 201 does not return to the original state (meandering state) as shown in FIG. 4A, but maintains the shortened state.

The positioning portion 90 may be in contact with the peripheral region of the entrance 203, for example, by sliding as indicated by the arrow C in FIG. 4C. In this case, the lumen 201 tends to be elongated in the direction opposite to the pulling direction. In other words, the lumen 201 will return to its original state. The insertion portion 62 including the positioning portion 90 is to be pulled to an inner part of the lumen 201 (tends to advance in the lumen 201). However, the positioning portion 90 is already in contact with the positioning portion of the entrance 203. By the contact, the insertion portion 62 is not pulled into the inner part of the lumen 201 (does not advance), and the lumen 201 is not elongated to return to the original state (meandering state) as shown in FIG. 4A, but maintains the shortened state.

The first through hole 92 (inside diameter D1 of the positioning portion 90) is minutely smaller than the outside diameter D2 of the insertion portion 62, and the positioning portion 90 has a desired thickness. The inside diameter D1 and the thickness are desirably adjusted, and the fixing force becomes greater than the elongation force of the lumen 201 by the adjustment. Accordingly, the positioning portion 90 ensures the fixing force by which the positioning portion 90 is fixed to the insertion portion 62. Thus, the insertion portion 62 is prevented from sliding the positioning portion 90 by the fixing force without being affected by the elongation force of the lumen 201, the insertion portion 62 is prevented from being shifted with respect to the positioning portion 90, and the insertion portion 62 is prevented from being inserted into the lumen 201 alone. The positioning portion 90 is continued to be positioned to the entrance 203 and the insertion portion 62 by the fixing force without being shifted with respect to the insertion portion 62. That is, even if the elongation force of the lumen 201 is applied to the insertion portion 62 and the positioning portion 90 through the insertion portion 62, the positioning portion 90 is positioned to the insertion portion 62 without being shifted with respect to the insertion portion 62 by the fixing force.

The insertion portion 62 is prevented from being inserted (pulled) into the lumen 201 by elongation of the lumen 201 indicated by the arrow D in FIG. 4C, by the positioning portion 90 which is in contact with the peripheral region of the entrance 203. Namely, the insertion device 60 is prevented from moving toward the insertion direction of the insertion device 60 by the positioning portion 90.

In the case where the state and the length of the lumen 201 is temporarily maintained in the shortened state as shown in FIG. 4B, the positioning portion 90 is in contact with the peripheral region of the entrance 203 by the elongation force of the lumen 201 in the opposite direction to the pulling caused in the lumen 201 as shown in FIG. 4C. Then, the positioning portion 90 is positioned at the second position 302 which is the entrance 203, as shown in FIG. 4C. That is in the state where the lumen 201 is pulled toward the entrance 203 by the insertion portion 62 through the fixing portion 70, as shown in FIG. 4B, the positioning portion 90 is positioned at the second position 302, as shown in FIG. 4C.

In other words, the insertion portion 62 is fixed at the first position by the fixing portion 70, and shortens the lumen 201 by applying a pulling force toward the entrance 203 of the lumen 201 from the first position. Then, when the positioning portion 90 is in contact with the peripheral region of the entrance 203 by the elongation force of the shortened lumen 201, the positioning portion 90 is positioned at the second position.

When the positioning portion 90 is positioned at the second position 302 which is the entrance 203, as shown in FIG. 4C, the positioning portion 90 and the fixing portion 70 sandwich the lumen 201 from the first position 301 to the entrance 203. As shown in FIG. 4C, the insertion device 60 controls (defines) the state and the length of the lumen 201 from the first position 301 to the entrance 203 by sandwiching, and positions the lumen 201 from the first position 301 to the entrance 203 by sandwiching. As shown in FIG. 4C, the insertion device 60 controls (defines) the state and the length of the insertion portion 62 from the first position 301 to the entrance 203 by sandwiching, and positions the insertion portion 62 from the first position 301 to the entrance 203 by sandwiching. The state of the insertion portion 62 indicates, for example, a bending shape from the first position 301 to the entrance 203. As stated above, the state and the length of the lumen 201 and the state and the length of the insertion portion 62 from the first position 301 to the entrance 203 are maintained as desirably controlled by the fixing portion 70 and the positioning portion 90. Accordingly, the lumen 201 is prevented from moving relative to the inside or the body, and is fixed. The state is confirmed, for example, by visual observation through X-ray observation, movement of the insertion device 60, and the length of the insertion device 60 exposed from the lumen 201.

As stated above, the lumen 201 itself is easily and stably fixed inside the body by the fixing portion 70 and the positioning portion 90. In other words, the lumen 20L is sandwiched by the fixing portion 70 and the positioning portion 90, and the state and the length of the lumen 201 are controlled by the fixing portion 70, the positioning portion 90, and the pulling of the lumen 201. The lumen 201 is fixed inside the body in the state where the state and the length thereof is controlled. Along with fixing of the lumen 201, the insertion device 60 fixed in the lumen 201 and at the entrance 203 is stably fixed. The insertion device 60 itself is easily fixed by expansion of the fixing portion 70, shortening of the lumen 201 through the fixing portion 70 by pulling of the insertion device 60, and bringing the positioning portion 90 into contact with the peripheral region of the entrance 203 by elongation of the lumen 201.

Accordingly, in the present embodiment, the lumen 201 can be fixed, and the insertion device 60 is prevented from being unintentionally inserted and removed relative to the lumen 201 by movement of the lumen 201. In the present embodiment, it is possible to prevent the insertion device GO itself from shifting, and to stably operate the insertion device 60. In particular, the positioning portion 90 can prevent the proximal end portion of the insertion device 60 exposed from the lumen 201 from shifting, and accordingly, the operation of the insertion device 60 can be stabilized. In the present embodiment, part of the insertion device 60 positioned outside of the lumen 201 is fixed by the positioning portion 90, and accordingly, the operation of the insertion device 60 outside of the lumen 201 can be stabilized.

By the aforementioned features, it is possible to bring the distal end portion of the insertion portion 12a of the endoscope 12 as shown in FIG. 4C and a treatment tool not shown in the drawings to approach an affected part 400 easily and stably, and to stably observe and treat the affected part 400.

In the present embodiment, when the fixing portion 70 and the positioning portion 90 sandwich the lumen 201 from the first position 301 to the entrance 203, the fixing portion 70 is in direct contact with the inner wall, etc. of the lumen 201, and the positioning portion 90 is in direct contact with the peripheral region of the entrance 203. Accordingly, in the present embodiment, the state and the length of the lumen 201 from the first position 301 to the entrance 203 is reliably controlled.

In the present embodiment, it is possible to accomplish a simple and down-sized structure at low cost.

The positioning portion 90 is detachable and attachable with respect to the insertion portion 62, and if the positioning portion 90 is not used, the positioning portion 90 is detached from the insertion portion 62. Accordingly, the positioning portion 90 does not obstruct the operation of the insertion device 60 and the endoscope 12.

The positioning portion 90 is positioned to the insertion portion 62 by the fixing force; however, the way of positioning is not limited thereto if the positioning portion 90 is positioned to the insertion portion 62. For example, convex parts and corresponding concave parts may be provided on the inner peripheral surface of the positioning portion 90 and the outer peripheral surface of the insertion portion 62.

[Modification]

The modification of the positioning portion 90 will be explained below. The positioning portion 90 according to the first embodiment may be combined with a positioning portion 90 in the modification as explained below.

As a modification shown in FIG. 5A, FIG. 5B, and FIG. 5C, the positioning portion 90 has a cut-out portion 96 consecutive to the notching portion 94, provided on the outer peripheral surface of the positioning portion 90, and formed by cutting a part of the outer peripheral surface out in an arc-shape, for example. The cut-out portion 96 is formed by depressing a part of the outer peripheral surface toward the inner peripheral surface. The shape and the diameter D3 of the cut-out portion 96 are substantially the same as the outer shape and the outside diameter D2 of the insertion portion 62, for example.

In the modification, since the diameter D3 of the cut-out portion 96 is substantially the same as the outside diameter D2 of the insertion portion 62, the insertion portion 62 can be fitted into the cut-out portion 96 when the positioning portion 90 is attached to the insertion portion 62, and the insertion portion 62 can be easily brought into contact with the notching portion 94. Accordingly, in the modification, the positioning portion 90 can be easily attached to the insertion portion 62 even one-handed.

Figure 6A:
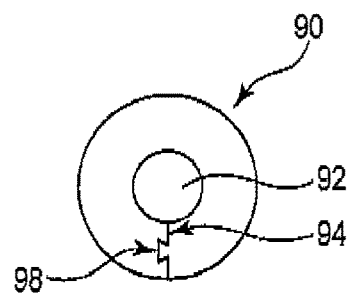
FIG. 6A is a front view of a positioning portion in the second modification.
Figure 6B:
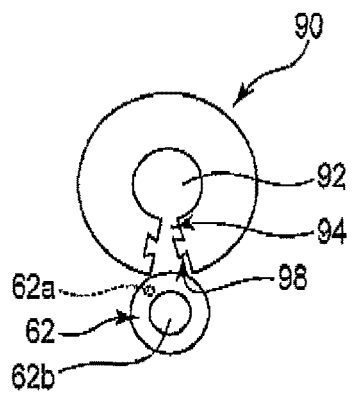
FIG. 6B illustrates where the positioning portion shown in FIG. 6A is to be attached to the insertion portion.
Figure 6C:
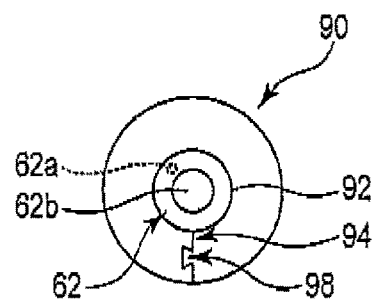
FIG. 6C illustrates where the positioning portion shown in FIG. 6A has been attached to the insertion portion.

As a second modification shown in FIG. 6A, FIG. 6B, and FIG. 6C, the positioning portion 90 has a fitting portion 98 provided to the notching portion 94 and used to fit both sides of the notching portion 94. The fitting portion 98 has a convex part provided on a surface of the notching portion 94 and a concave part provided on another surface of the notching portion 94 and fits the convex part. The shapes of the convex part and the concave part are not limited.

Figure 7:
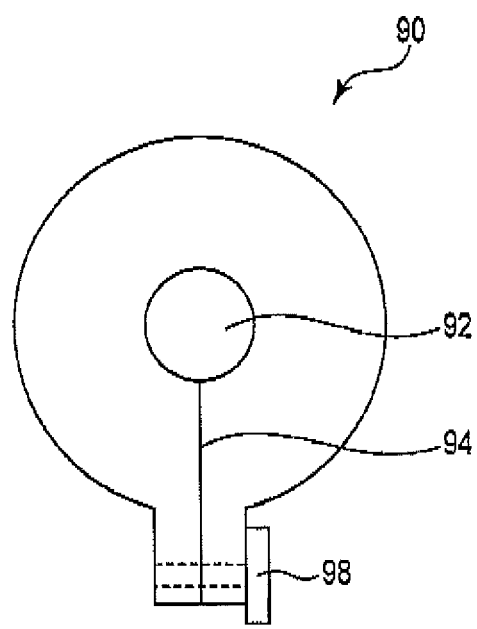
FIG. 7 is a front view of a positioning portion in the third modification.

In the present modification, the fitting portion 98 can prevent the positioning portion 90 from being unintentionally removed from the insertion portion 62. The fitting portion 98 is not limited to the aforementioned shape. As shown in FIG. 7, the fitting portion 98 may have a screw member provided on a convex part of the positioning portion 90 that is screwed into the notching portion 94. The convex part of the positioning portion 90 is provided as projecting toward the outside, and includes a part of the notching portion 94. In addition, the fitting portion 96 may, for example, have a hook and loop fastener and a binding band not shown in the drawings.

Second Embodiment

Figure 8A:
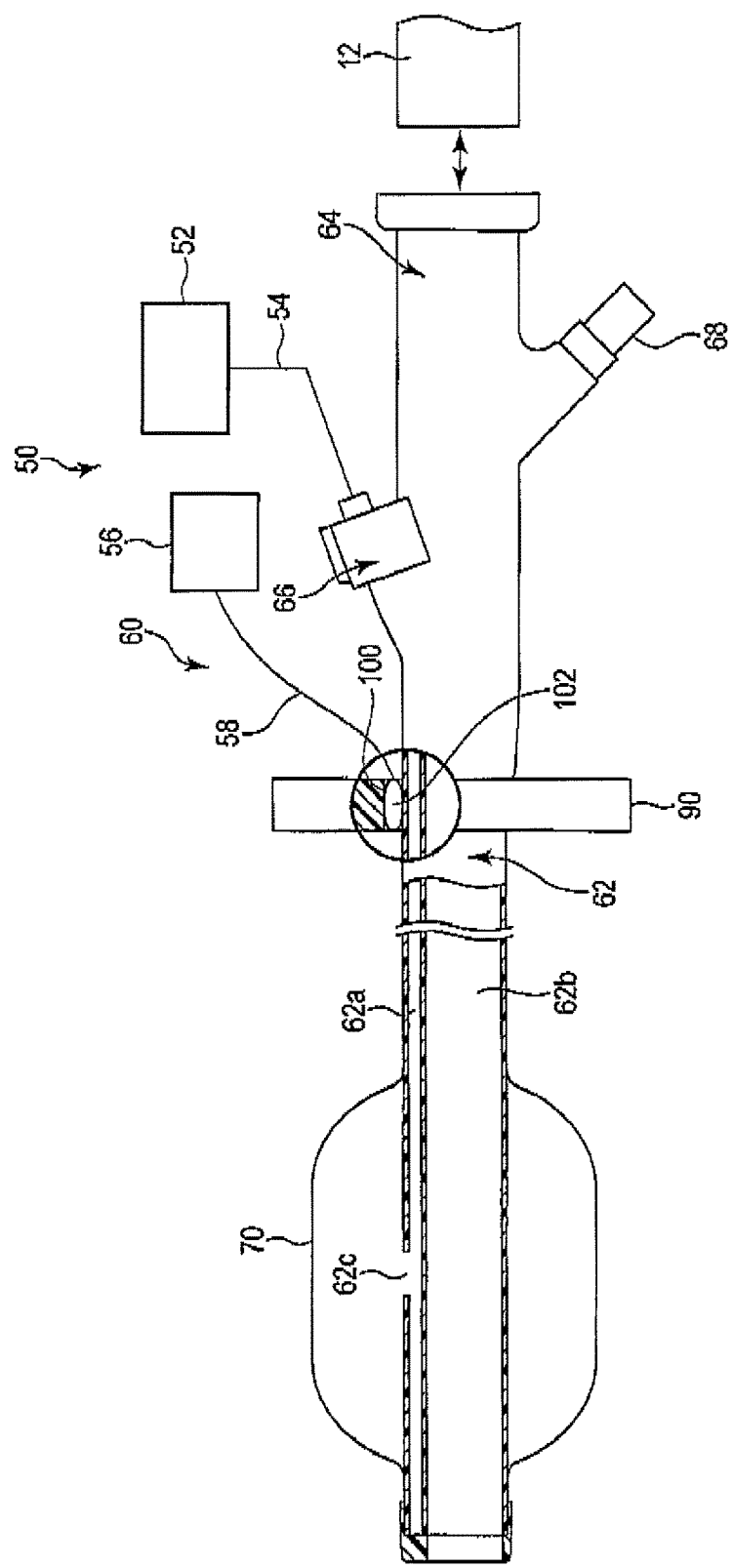
FIG. 8A is a schematic view of an insertion assistance unit in the second embodiment.
Figure 8B:
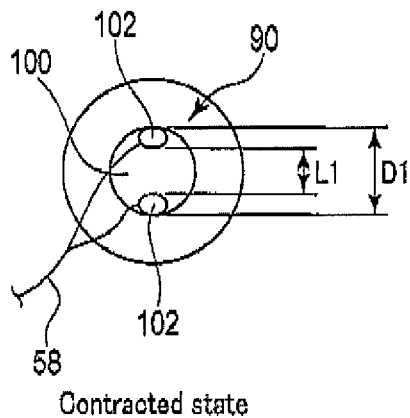
FIG. 8B is a front view of the positioning portion of the second embodiment and illustrates the state before a shape deformation portion is deformed.
Figure 8C:
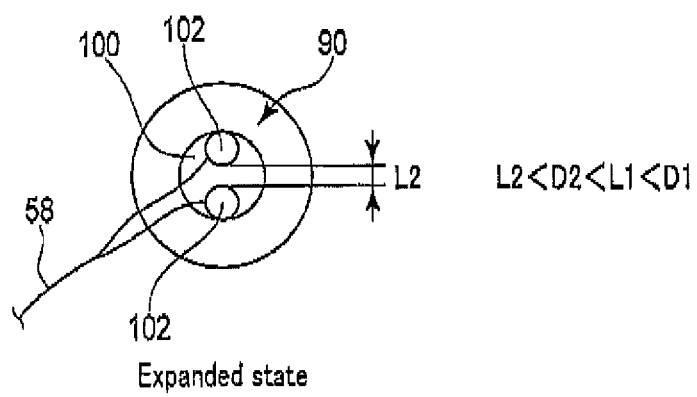
FIG. 8C illustrates the state after the shape deformation portion shown in FIG. 8B is deformed.

With reference to FIG. 8A, FIG. 8B, and FIG. 8C, the parts different from the first embodiment will be explained below.

As shown in FIG. 8A, the insertion assistance unit 50 includes a third fluid pump 56, and a third fluid supply-drainage tube 58 which is connected to the third fluid pump 56. The third fluid pump 56 has a switching unit not shown in the drawings, such as a foot switch that switches between supply and drainage of fluid.

As shown in FIG. 8A, FIG. 8B, and FIG. 8C, the positioning portion 90 includes a second through hole 100 that passes through the positioning portion 90 in the thickness direction of the positioning portion 90. The second through hole 100 is provided at a center of the positioning portion 90. The positioning portion 90 is formed, for example, as a ring shape. The external shape of the positioning portion 90 is not limited, if the second through hole 100 is provided. The second through hole 100 is formed so that the insertion portion 62 passes through the positioning portion 90 in the thickness direction of the positioning portion 90. The second through hole 100 of the present embodiment (inside diameter D1 of the positioning portion 90) is minutely larger than the outside diameter D2 of an insertion portion 62.

As shown in FIG. 8A, FIG. 8B, and FIG. 8C, the positioning portion 90 has two shape deformation portions 102 provided to the second through hole 100. When the insertion portion 62 passes through the second through hole 100, and the positioning portion 90 is positioned at the insertion portion 62, the shape deformation portions 102 are deformed so that the shape deformation portions 102 are in contact with the outer peripheral surface of the insertion portion 62. When the insertion portion 62 is inserted to the second through hole 100, which is formed to be larger than the outside diameter of the insertion portion 62 to allow the insertion portion 62 to pass through, the shape deformation portions 102 are deformed in the second through hole 100 to fix the insertion portion 62 at the second through hole 100. The shape deformation portions 102 have a balloon that is expanded and contracted by supply or drainage when fluid is supplied and drained relative to the third fluid pump 56 to the shape deformation portions 102 through the third fluid supply-drainage tube 58. Specifically, the shape deformation portions 102 expand if gas is supplied to the shape deformation portions 102, and contract if gas is emitted from the shape deformation portions 102, for example. The shape deformation portions 102 is deformed by expansion and contraction of the shape deformation portions 102.

In the state where the insertion portion 62 passes through the second through hole 100, if the shape deformation portions 102 are expanded, the shape deformation portions 102 are brought into pressure contact with the outer peripheral surface of the insertion portion 62 by the expansion. Accordingly, the positioning portion 90 is positioned at the insertion portion 62. The expansion degree of the shape deformation portions 102 is controlled by the third fluid pump 56.

In the state where the insertion portion 62 passes through the second through hole 100, if the shape deformation portions 102 are contracted, the pressure contact is released by contraction. Accordingly, the positioning portion 90 becomes slidable on the insertion portion 62 in the axial direction of the insertion device 60.

FIG. 8B and FIG. 8C show two shape deformation portions 102. However, it is sufficient if at least one shape deformation portion 102 is provided. When a plurality of shape deformation portions 102 are provided, the shape deformation portions 102 are spaced at regular intervals in a peripheral direction of the second through hole 100. It is desirable that two shape deformation portions 102 are provided, for example. The shape deformation portions 102 are fixed on the inner peripheral surface of the positioning portion 90 by adhesion, for example.

When two shape deformation portions 102 are provided, the relationships as indicated below are suitable.

As shown in FIG. 8B, the size of the second through hole 100 (inside diameter D1 of the positioning portion 90) is represented as D1.

As shown in FIG. 8C, in the state where the shape deformation portions 102 are contracted, the interval (length) between the shape deformation portions 102 in a radial direction of the second through hole 100 is represented as L1.

As shown in FIG. 8C, in the state where the shape deformation portions 102 are expanded, the interval (length) between the shape deformation portions 102 in the radial direction of the second through hole 100 is represented as L2.

Similar to the first embodiment, the outside diameter of the insertion portion 62 is represented as D2.

In this case, the relationship of L2<D2<L1<D1 is satisfied.

In the present embodiment, since the shape deformation portions 102 can be easily expanded and contracted by a switching unit not shown in the drawings, the positioning portion 90 can easily slide and can be easily positioned, and sliding and positioning can be easily and quickly switched. In the present embodiment, if the positioning portion 90 slides, D2<L1 is satisfied. Accordingly, when the positioning portion 90 slides, it is possible to prevent the positioning portion 90, and the insertion portion 62 from being worn out by sliding.

In the present embodiment, one positioning portion 90 can be commonly used by various types of insertion portions 62 which are different in thickness.

Although it is not shown in the drawings, the shape deformation portion 102 may be removably provided relative to the second through hole 100, and formed of a ring-shaped resin material. In this case, even if the outer peripheral surface of the insertion portion 62 is unevenly formed, the shape deformation, portion 102 formed of a resin material can be deformed and positioned on the outer peripheral surface to match the unevenness.

Third Embodiment

Figure 9:
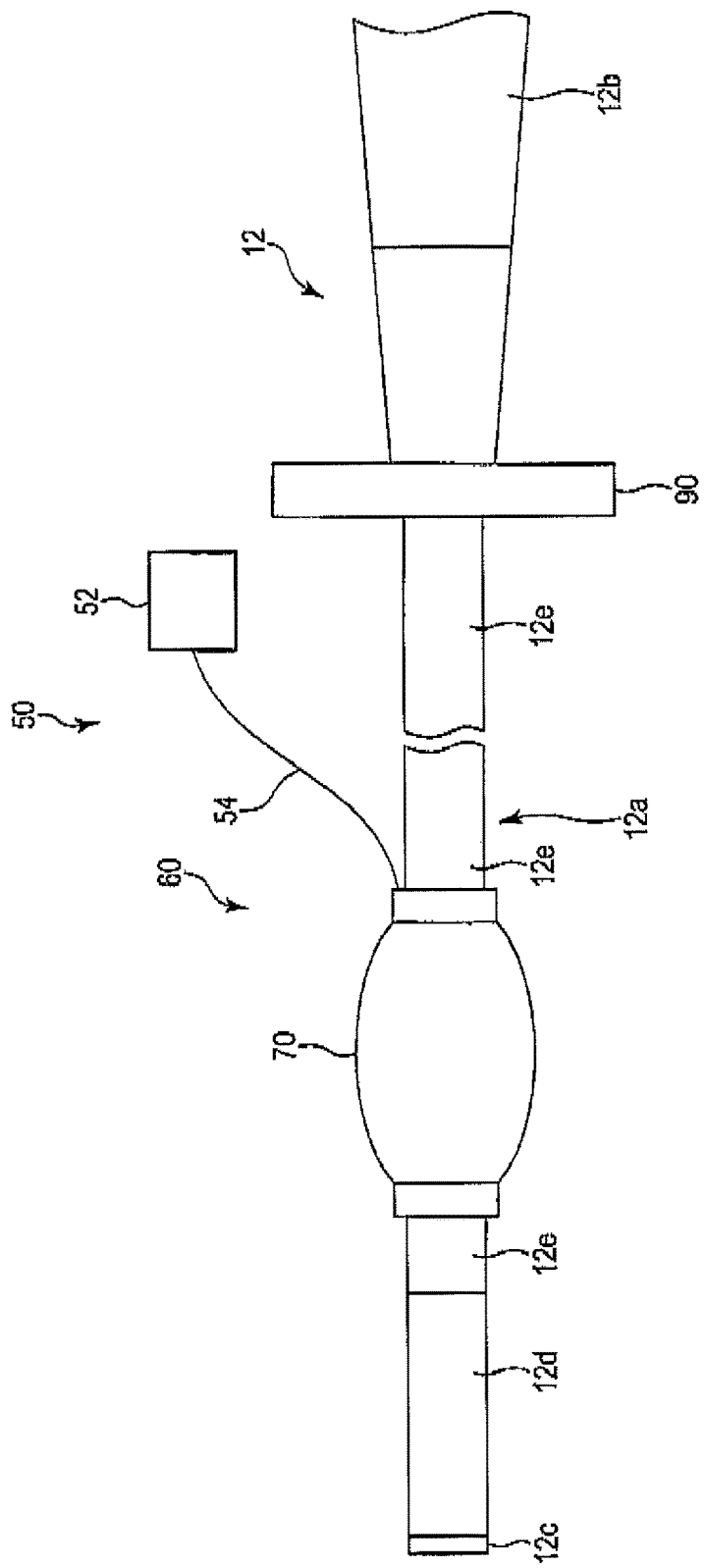
FIG. 9 is a schematic view of an insertion assistance unit in the third embodiment.

With reference to FIG. 9, the parts different from the first and second embodiments will be explained below.

The insertion device 60 of the present embodiment acts as the insertion portion 12a of the endoscope 12.

In this case, a fixing portion 70 and a positioning portion 90 are provided to a flexible tube portion 12e of an insertion portion 62. The fixing portion 70 is directly connected to a first fluid supply-drainage tube 54. The positioning portion 90 is removable relative to the flexible tube portion 12e. The inside diameter of the positioning portion 90 is minutely smaller than the outside diameter of the flexible tube portion 12e. Accordingly, the positioning portion 90 is positioned on the flexible tube portion 12e.

In the present embodiment, since the insertion device 60 functions as the insertion portion 12a of the endoscope 12, it is not necessary for the insertion portion 12a to be held with an over-tube, as in the first embodiment, and the insertion portion 12a can be directly held. This improves operability of the insertion device 60.

Fourth Embodiment

With reference to FIG. 10A, FIG. 10B, FIG. 10C, FIG. 10D, FIG. 10E, FIG. 10F, FIG. 10G, FIG. 10H, FIG. 10I, FIG. 10J, and FIG. 10K, the parts different from the first, second, and third embodiments will be explained below.

The insertion device 60 further includes a control unit 110 which controls the state of the insertion device 60 exposed externally to the lumen 201; specifically, the state of an insertion portion 62 that is positioned at the behind of the positioning portion 90. The state of the insertion portion 62 indicates, for example, a bending shape. The control unit 110 is positioned at the behind of the positioning portion 90.

Figure 10A:
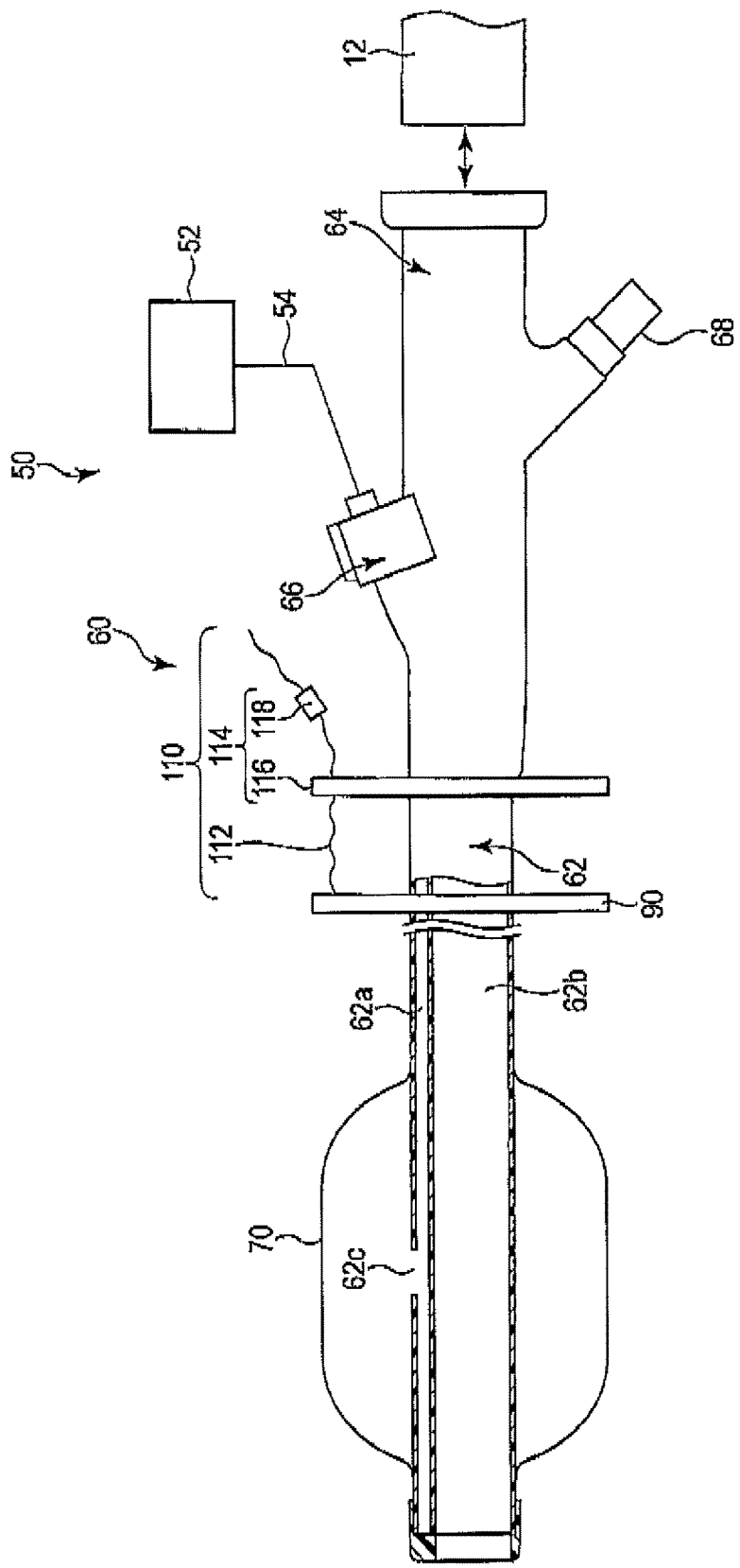
FIG. 10A is a schematic view of an insertion assistance unit in the fourth embodiment.

As shown in FIG. 10A, FIG. 10T, and FIG. 10K, the control unit 110 includes an actuation portion 112 to which tension is applied in the state where the state of the insertion portion 62 is temporarily controlled, and a state maintenance portion 114 that controls the state of the insertion portion 62 by maintaining the state where tension is applied to the actuation portion 112.

The actuation portion 112 is provided between the state maintenance portion 114 and the positioning portion 90. The state maintenance portion 114 and the positioning portion 90 are slipped on the insertion portion 62 outside of the lumen 201 and at any position of the insertion portion 62.

Figure 10B:
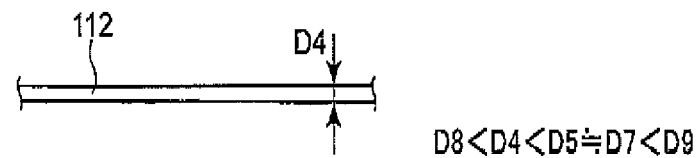
FIG. 10B is a side view of an actuation portion.
Figure 10C:
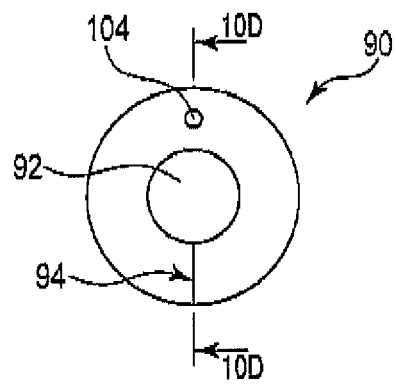
FIG. 10C is a front view of a positioning portion in the fourth embodiment.
Figure 10D:
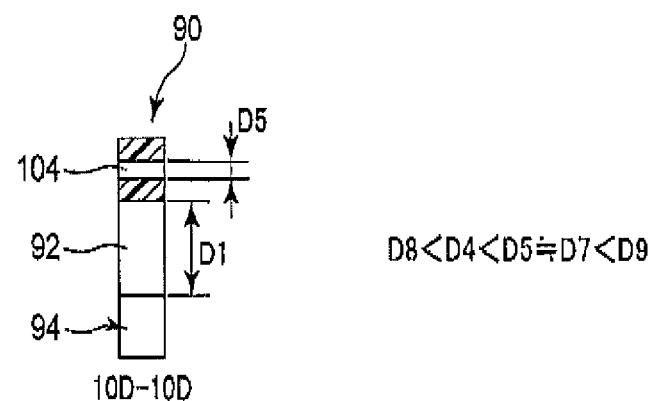
FIG. 10D is a cross-sectional view of the positioning portion taken along line 10D-10D shown in FIG. 10C.
Figure 10E:
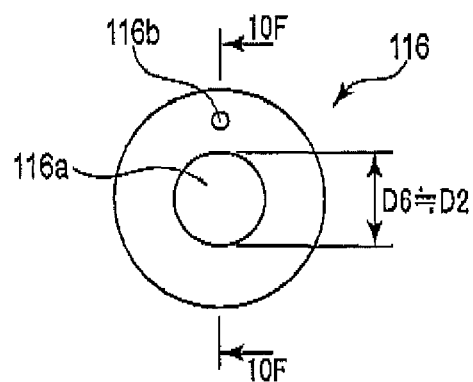
FIG. 10E is a front view of a main portion.
Figure 10F:
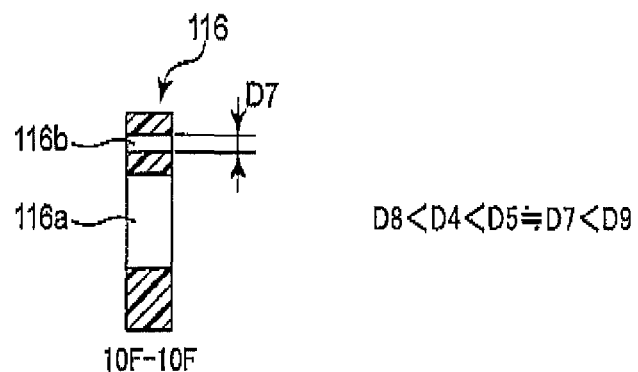
FIG. 10F is a cross-sectional view of the main portion taken along line 10E-10F shown in FIG. 10E.
Figure 10G:
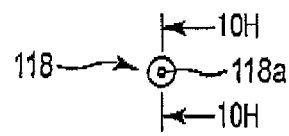
FIG. 10G is a front view of a contact maintenance portion.
Figure 10H:
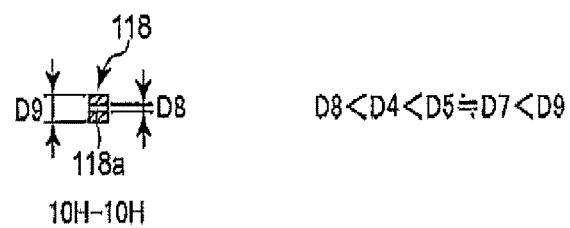
FIG. 10H is a cross-sectional view of the contact maintenance portion taken along line 10H-10H shown in FIG. 10G.

The actuation portion 112 included a bendable linear member having one end portion that acts as a fixing end portion to be fixed to the positioning portion 90 and an other end portion that acts as a free end portion. The one end portion is, for example, inserted into a hole 104 provided on the positioning portion 90, and fixed to the hole 104 by adhesion. Since the positioning portion 90 is formed of an elastic member, even when the diameter D4 of the actuation portion 112 is minutely smaller than the diameter D5 of the hole 104, the actuation portion 112 can be inserted into the hole 104 by, for example, plunging the metallic actuation portion 112 to expand the hole 104, as shown in FIG. 10B, FIG. 10C, and FIG. 10D. By this operation, the actuation portion 112 is adhesively fixed to the contracted positioning portion 90. As shown in FIG. 10D, the diameter D5 of the hole 104 is smaller than the first through hole 92 (inside diameter D1 of the positioning portion 90). The other end portion is provided at the behind of the positioning portion 90. The actuation portion 112 is a thin material. The actuation portion 112 has a desired hardness. Even if the insertion portion 62 exposed externally to the lumen 201 is meandering, the meandering state of the insertion portion 62 is controlled by the hardness of the actuation portion 112 when tension is applied to the actuation portion 112. Such an actuation portion 112 is formed of, for example, a metal such as stainless steel, or of cotton, vinyl chloride, rubber, etc.

As shown in FIG. 10A, FIG. 10E, FIG. 10F, FIG. 10G, FIG. 10H, FIG. 10J, and FIG. 10K, the state maintenance portion 114 includes a main portion 116 that includes a third through hole 116a and a fourth through hole 116b, and a contact maintenance portion 118 that maintains the state where tension is applied to the actuation portion 112 by bringing into contact with the main portion 116, when tension is applied to the actuation portion 112 in the state where the state of the insertion portion 62 is temporarily controlled.

The third through hole 116a is formed so that the main portion 116 is slipped on the insertion portion 62, and the insertion portion 62 passes through the main portion 116 in the thickness direction of the main portion 116. Accordingly, the diameter D6 of the third through hole 116a is substantially the same as the diameter D2 of the insertion portion 62. The third through hole 116a is independent from the other forth through hole 116b, and is larger than the fourth through hole 116b.

The fourth through hole 116b is formed such that the actuation portion 112 passes through the main portion 116 in the thickness direction of the main portion 116, and the actuation portion 112 is movable into the main portion 116 in the thickness direction of the main portion 116. Thus, the diameter D7 of the fourth through hole 116b is larger than the diameter D4 of the actuation portion 112. The diameter D7 of the fourth through hole 116b is substantially the same as the diameter D5 of the hole 104.

The external shape of the main portion 116 is not particularly limited if the third through hole 116a and the fourth through hole 116b are provided.

The main portion 116 is fixed to the insertion portion 62 at the behind of the positioning portion 90 by adhesion, for example. For example, it is suitable that the main portion 116 is fixed close to an operation portion 64.

The contact maintenance portion 118 has a fifth through hole 118a that passes through the contact maintenance portion 118 in the thickness direction of the contact maintenance portion 118. The contact maintenance portion 118 is formed, for example, as a ring shape. If the fifth through hole 118a is provided, the external shape of the contact maintenance portion 118 is not particularly limited. The fifth through hole 118a is formed so that the contact maintenance portion 118 is slipped on the actuation portion 112, and the actuation portion 112 passes through the contact maintenance portion 118 in the thickness direction of the contact maintenance portion 118. The fifth through hole 118a (inside diameter D8 of the contact maintenance portion 118) of the present embodiment is minutely smaller than the diameter D4 of the actuation portion 112. Accordingly, the inner peripheral surface of the contact maintenance portion 118 is assuredly fixed to the outer peripheral surface of the actuation portion 112. The contact maintenance portion 118 has a desired thickness, and a wide contact area is ensured by the thickness. Thus, when the contact maintenance portion 118 is attached to the actuation portion 112, the contact maintenance portion 118 is adhesively positioned and fixed to the actuation portion 112. The contact maintenance portion 118 is accordingly disposed to the actuation portion 112. In other words, the contact maintenance portion 118 ensures a fixing force by which the contact maintenance portion 116 is fixed to the actuation portion 112. If a force equal to or stronger than the fixing force (contacting force) is applied to the contact maintenance portion 118 in the axial direction of the actuation portion 112, for example, the contact maintenance portion 118 is slidable along the actuation portion 112 in the axial direction of the insertion portion 112. The contact maintenance portion 118 is slidable relative to the actuation portion 112 in the axial direction of the actuation portion 112, and has a fixing force to be positioned and fixed to the actuation portion 112 in the state where the contact maintenance portion 118 is in contact with the main portion 116.

Such an actuation portion 112 is formed of a member having elastic properties, for example. Such a member has, for example, silicon rubber, fluorine rubber, and a thermoplastic elastomer such as polyurethane. The shape of the actuation portion 112 is not limited if the above structures are achieved.

The diameter D9 of the contact maintenance portion 118 is larger than the diameter D7 of the fourth through hole 116b. Thus, the contact maintenance portion 118 is brought into contact with the main portion 116, but does not pass through the main portion 116 through the fourth through hole 116b. The contact maintenance portion 118 is not disposed between the main portion 116 and the positioning portion 90, but is disposed in the behind of the main portion 116. The contact maintenance portion 118 maintains the state where tension is applied to the actuation portion 112 by bringing into contact with the main portion 116, and the contact maintenance portion 118 controls the state of the insertion portion 62, when tension is applied to the actuation portion 112 in the state where the state of the insertion portion 62 is temporarily controlled. By the above operation, the relationships of $D8<D4<D5 \cong D7<D9$ are satisfied.

In the present embodiment, the operation from expansion of the first fixing portion 70 to the positioning portion 90 being in contact with the peripheral region of the entrance 203 is the same as that in the first embodiment. The operation explained below is performed after the operation of the first embodiment as shown in FIGS. 4A, 4B, and 4C.

Figure 10I:
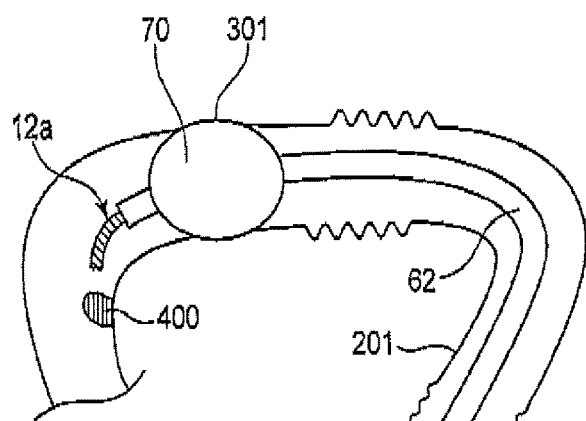
FIG. 10I illustrates the state where the insertion portion exposed externally to a lumen is desirably bent so that the insertion portion is adjacent to the peripheral region of the entrance after the state shown in FIG. 4C.
Figure 10I:
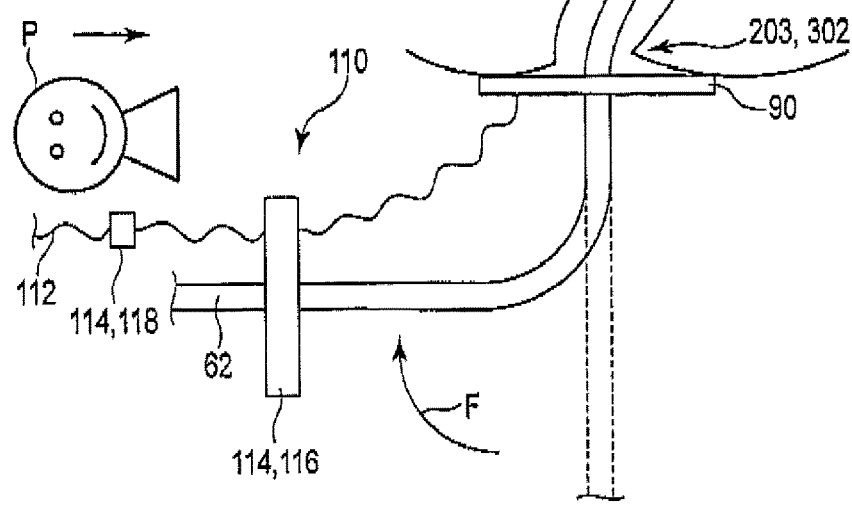

If the insertion portion 62 is desirably bent as shown by an arrow F in FIG. 10I, the proximal end portion side of the insertion portion 62 exposed externally to the lumen 201 faces an operator P who operates an insertion system 10, for example. The actuation portion 112 is bent at this time.

Figure 10J:
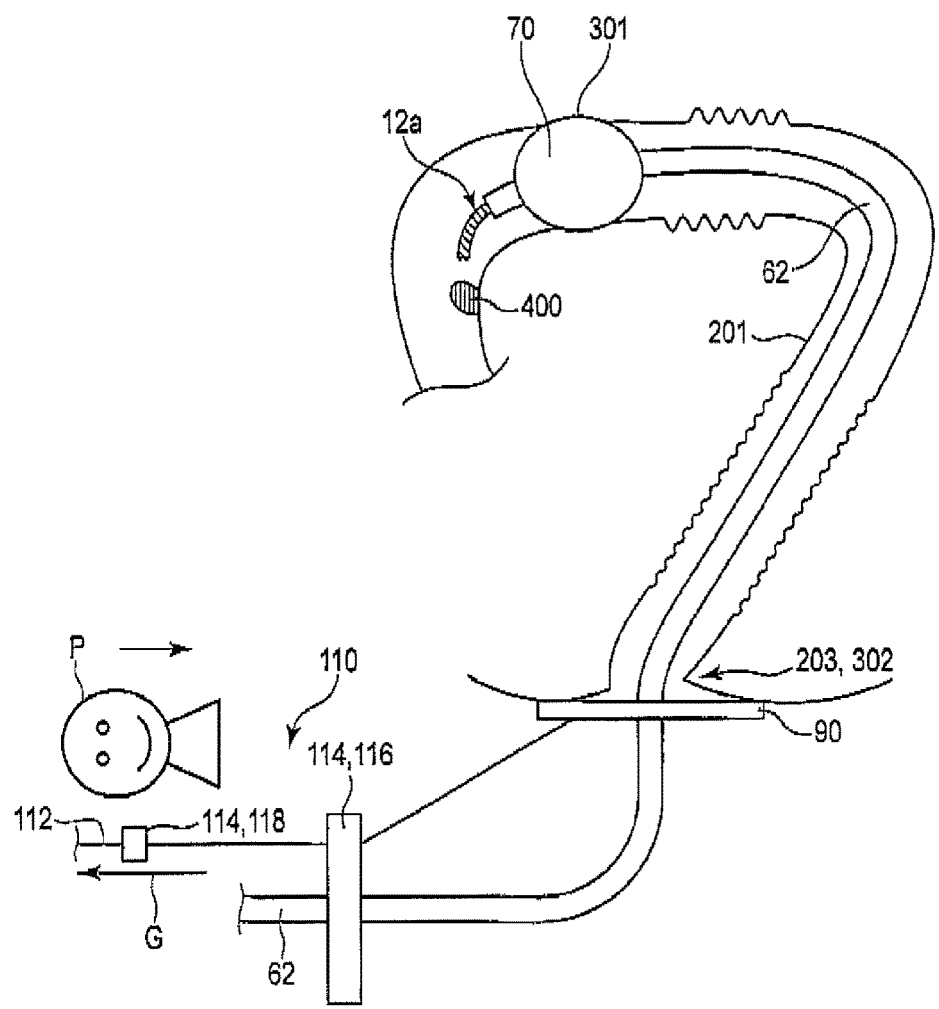
FIG. 10J illustrates the state where the actuation portion is pulled to the operation portion side, and tension is applied to the actuation portion after the state shown in FIG. 10I.

In this state, the actuation portion 112 is pulled to the operation portion 64 side as shown by an arrow G in FIG. 10J, and tension is applied to the actuation portion 112. In this case, the actuation portion 112 is controlled as a linear state, for example.

Then, the contact maintenance portion 118 slides on the actuation portion 112 as shown by an arrow H in FIG. 10K, and is brought into contact with the main portion 116. The contact maintenance portion 118 is positioned and fixed to the actuation portion 112 in the state of contact. By this operation, the actuation portion 112 is maintained as the state where tension is applied to the actuation portion 112 (tensioned state).

Accordingly, the state (bending shape) of the insertion portion 62 exposed externally to the lumen 201 is controlled, and the insertion portion 62 is positioned adjacent to the peripheral region of the entrance 203.

Accordingly, in the present embodiment, the operator P can easily operate the insertion device 60, for example, by his right hand, in the state where the proximal end portion side of the insertion portion 62 faces the operator P standing by a patient, and the operator P can visually observe the patient and the insertion portion 62. Since the state (bending shape) of the insertion portion 62 is controlled, shifting of the insertion portion 52 is prevented. Accordingly, since the insertion device 60, the state of which is controlled, is operated, the insertion device 60 and the endoscope 12 can be stably operated.

The main portion 116 and the contact maintenance portion 118 are disposed so that the actuation portion 112 can maintain the tensioned state. However, if the actuation portion 112 maintains the tensioned state, the configuration of the control unit 110 is not limited to the aforementioned configuration. The actuation portion 112 may be fixed to the proximal end portion of the insertion portion 62. In this case, the actuation portion 112 maintains the tensioned state by the positioning portion 90.

The actuation portion 112 is relatively movable to at least one of the state maintenance portion 114 and the positioning portion 90, or is fixable at any position of at least one of the state maintenance portion 114 and the positioning portion 90.

For example, as shown in FIG. 10I, when the insertion portion 62 is beat, the other end portion side of the actuation portion 112 is fixed at any position relative to the state maintenance portion 114, and the actuation portion 112 between the positioning portion 90 and the main portion 116 moves relative to the positioning portion 90 by the bending of the insertion portion 62. As shown in FIG. 10J, when the actuation portion 112 is pulled to the operation portion 64 side, the other end portion side of the actuation portion 112 moves backward relative to the main portion 116 by the pulling, and the one end portion side of the actuation portion 112 is fixed to the positioning portion 90. In the state shown in FIG. 10J, the actuation portion 112 between the positioning portion 90 and the main portion 16 moves backward relative to the main portion 116 of the state maintenance portion 114 and the positioning portion 90 by the pulling. In the state shown in FIG. 10K, the actuation portion 112 is fixed to the main portion 116 of the state maintenance portion 114 and the positioning portion 90.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device for insertion into an intestinal tract, the insertion device being configured to be positioned relative to both of a first position inside of the intestinal tract and a second position outside of the intestinal tract, the insertion device comprising:
    an insertion portion that includes a distal end and a proximal end in an axial direction, and includes:
        a part having a fixing portion that is arranged at the distal end to be inserted into the intestinal tract, and is configured to fix the distal end side to the intestinal tract at the first position,
        a part arranged at the proximal end side relative to the part having the fixing portion, and is not configured to be fixed to the intestinal tract inside of the intestinal tract, and
        a part configured to be arranged outside of the intestinal tract; and
    a positioning portion that is formed of an elastic member in a ring shape so as to form a through hole through which the insertion portion passes inside, the positioning portion being slideable relative to the insertion portion, the positioning portion comprising a slit portion extending from the through hole along a radial direction of the positioning portion, the positioning portion being attached to the part of the insertion portion configured to be arranged outside of the intestinal tract, the positioning portion being configured to position the insertion portion at the second position, and the positioning portion being detachable and attachable relative to the insertion portion via the slit portion,
    wherein
        the insertion portion is configured to apply a force of pulling the intestinal tract from the first position fixed by the fixing portion to an entrance side of the intestinal tract to shorten the intestinal tract when the insertion portion is pulled in a removal direction, and
        the positioning portion is fixed to the insertion portion by a force stronger than an elongating force of the shortened intestinal tract when the positioning portion is positioned at a peripheral region of an entrance of the intestinal tract while being in contact with the peripheral region.

2. The insertion device according to claim 1, wherein
    when the positioning portion is fixed at the second position, the positioning portion sandwiches the intestinal tract with the fixing portion fixed at the first position, and
    the insertion device is configured to:
        control a state and a length of the intestinal tract from the first position to the entrance by the sandwiching,
        position the intestinal tract from the first position to the entrance by the sandwiching,
        control a state and a length of the insertion portion from the first position to the entrance by the sandwiching, and
        position the insertion portion from the first position to the entrance by the sandwiching.

3. The insertion device according to claim 2, further comprising a control unit that controls a state of the insertion portion relative to the insertion portion positioned at the behind of the positioning portion.

4. The insertion device according to claim 3, wherein the control unit comprises:
    an actuation portion to which tension is applied in a state where the state of the insertion portion is temporarily controlled; and
    a state maintenance portion that maintains a state where tension is applied to the actuation portion to control the state of the insertion portion.

5. The insertion device according to claim 4, wherein
    the actuation portion includes a linear member, and
    the actuation portion is disposed between the positioning portion and the state maintenance portion that are slipped to the insertion portion at a discretionary position of the insertion portion and outside of the intestinal tract, and is relatively movable to at least one of the state maintenance portion and the positioning portion, or is fixable at a discretionary position of at least one of the state maintenance portion and the positioning portion.

6. The insertion device according to claim 4, wherein
    the actuation portion includes a linear member having one end portion fixed to the positioning portion and an other end,
    the state maintenance portion includes:
        a main portion that includes a through hole through which the insertion portion passes and an other through hole through which the actuation portion passes and moves, and is fixed to the insertion portion in the behind of the positioning portion, and
        a contact maintenance portion larger than the other through hole that is disposed to the actuation portion, and maintains a state where tension is applied to the actuation portion by bringing into contact with the main portion, when tension is applied to the actuation portion in a state where the state of the insertion portion is temporarily controlled.

7. The insertion device according to claim 6, wherein the fixing portion has a balloon that is expanded and contracted.

8. The insertion device according to claim 1, wherein a diameter of the through hole of the positioning portion is smaller than an outside diameter of the insertion portion.

9. The insertion device according to claim 1, wherein the positioning portion further includes a cut-out portion formed by cutting a part of an outer peripheral surface out to be consecutive to the slit portion.

10. The insertion device according to claim 9, wherein the shape of the cut-out portion is substantially equal to a part of an external shape of the insertion portion.

11. The insertion device according to claim 1, wherein the positioning portion further includes a fitting portion that fits both sides of the slit portion.

12. The insertion device according to claim 1, wherein the positioning portion includes a shape deformation portion that is deformed in a through hole to fix the insertion portion to the through hole, when the insertion portion is inserted to the through hole formed to be larger than an outside diameter of the insertion portion to allow the insertion portion to pass through.

13. The insertion device according to claim 12, wherein the shape deformation portion has a balloon that is expanded and contracted.

14. The insertion device according to claim 12, wherein the shape deformation portion is formed of a resin material.

15. The insertion device according to claim 1, wherein the fixing portion is configured to be fixed to the intestinal tract by friction generated between the fixing portion and the intestinal tract in a direction along an insertion direction of the insertion portion when the fixing portion is in contact with the intestinal tract.

16. The insertion device according to claim 1, acting as at least one of an over-tube, a catheter, and an insertion portion of an endoscope.

17. An insertion system comprising an endoscope and an insertion device according to claim 1 that is attached to the endoscope.

18. The insertion device according to claim 1, wherein the insertion device is inserted into the intestinal tract.

\* \* \* \* \*